United States Patent [19]
Rudnic et al.

[11] Patent Number: 5,897,876
[45] Date of Patent: Apr. 27, 1999

[54] EMULSIFIED DRUG DELIVERY SYSTEM

[75] Inventors: Edward M. Rudnic, North Potomac, Md.; John A. McCarty, Miami Springs, Fla.; George W. Belendiuk, deceased, late of Potomac, Md.; Beth A. Burnside, Silver Springs, Md.; Charlotte M. McGuinness, Bethesda, Md.; Krystyna Belendiuk, Potomac, Md., executrix of said George W. Belendiuk, deceased

[73] Assignee: Shire Laboratories Inc., Rockville, Md.

[21] Appl. No.: 08/879,994

[22] Filed: Jun. 20, 1997

Related U.S. Application Data

[62] Continuation of application No. 08/475,322, Jun. 7, 1995, abandoned, which is a continuation of application No. 08/424,521, filed as application No. PCT/US95/03393, Mar. 17, 1995, abandoned, which is a continuation of application No. 08/210,351.

[51] Int. Cl.$^6$ ............................ A61K 9/107; A61K 9/66; A61K 47/12
[52] U.S. Cl. .................... 424/455; 424/463; 514/784; 514/785; 514/786; 514/938; 514/943; 514/946; 514/962
[58] Field of Search ..................... 424/455, 463; 514/784, 785, 786, 938, 943, 946, 962

[56] References Cited

U.S. PATENT DOCUMENTS

| | | | |
|---|---|---|---|
| 4,083,973 | 4/1978 | van der Vies | 424/239 |
| 4,115,313 | 9/1978 | Lyon et al. | 252/309 |
| 4,330,338 | 5/1982 | Banker . | |
| 4,606,913 | 8/1986 | Aronson et al. . | |
| 4,690,775 | 9/1987 | Schott et al. | 252/312 |
| 4,784,845 | 11/1988 | Desai et al. | 424/80 |
| 4,869,897 | 9/1989 | Chatterjee et al. | 424/47 |
| 4,990,337 | 2/1991 | Kurihara et al. | 424/427 |
| 5,143,934 | 9/1992 | Lading et al. | 514/396 |
| 5,206,219 | 4/1993 | Desai | 514/3 |
| 5,342,625 | 8/1994 | Hauer et al. | 424/455 |

FOREIGN PATENT DOCUMENTS

| | | |
|---|---|---|
| WO 93/02664 | 2/1993 | WIPO . |
| WO 93/02665 | 2/1993 | WIPO . |
| WO 94/08605 | 4/1994 | WIPO . |

OTHER PUBLICATIONS

Constantinides et al., Formulation & Intestinal Absorption Enhancement Evaluation of Water–in–Oil Microemulsions Incorporating Medium–Chain Glycerides, *Pharm.Research.*, vol. 11, No. 10, pp. 1385–1390, (1994).

Ritschel et al., Improvement of Peroral Absorption of Cyclosporine A by Microemulsions, *Meth.Find.Exp.Clin.Pharmacol*, 12(2):127–134, (1990).

Shichiri et al., Increased Intestinal Absorption of Insulin in a Micellar Solution, *First Dept.of Medicine, Osaka Univ. Medical School*, pp. 175–183, (1977).

Ritschel, Microemulsions for Improved Peptide Absorption from the Gastrointestinal Tract, *Meth.Find.Exp.Clin.Pharmacol.*, 13(3): 205–220, (1991).

Kararli et al., Oral Delivery of a Renin Inhibitor Compound Using Emulsion Formulations, *Pharm.Research*, vol. 9, No. 7, pp. 888–893, (1992).

(List continued on next page.)

Primary Examiner—S. Mark Clardy
Attorney, Agent, or Firm—Elliot M. Olstein; Raina Semionow

[57] ABSTRACT

A pharmaceutical preparation comprising a stable, surface-active emulsion or dispersion of a pharmaceutical agent incorporated into an emulsion (i) having a hydrophobic discontinuous phase of a long chain carboxylic acid or ester or alcohol thereof dispersed in an aqueous phase or (ii) having a hydrophilic discontinuous phase dispersed in a hydrophobic phase of a long chain carboxylic acid or alcohol thereof. The emulsion with pharmaceutical agent is incorporated into a pharmaceutical carrier suitable for oral delivery.

24 Claims, 3 Drawing Sheets

OTHER PUBLICATIONS

Myers et al., Systemic Bioavailability of Penclomedine (NSC–338720) from Oil–in–Water Emulsions Administered Intraduodenally to Rats, *Int'l. Jnl. of Pharmaceutics,* 78:217–226, (1992).

Bhargava et al., Using Microemulsions for Drug Delivery, *Pharm.Tech.,* pp. 47–51, (Mar. 1987).

Sarciaux et al., Using Microemulsion Formulations for Oral Drug Delivery of Therapeutic Peptides, *Int'l. Jnl. of Pharmaceutics,* 120:127–136, (1995).

EMULSIFIED DRUG DELIVERY SYSTEM

This application is a continuation of application Ser. No. 08/475,322, filed Jun. 7, 1995, abandoned, which is a continuation of U.S. Ser. No. 08/424,521, filed Aug. 28, 1995, which is a 371 of PCT/US95/03393, filed Mar. 17, 1995 (abandoned), which is a continuation of U.S. Ser. No. 08/210,351, filed Mar. 18, 1994 (abandoned).

The ability of drugs to be administered via the oral route depends on several factors. The drug must be soluble in the gastrointestinal fluids in order for the drug to be transported across biological membranes, or be suitable for an active transport mechanism. Very small particulates (less than 300 nanometers) can be absorbed through the lymphatic system via the Peyer's Patch system in the intestinal tract. However, this mechanism is not capable of absorbing large doses of drugs into the systemic circulation.

A problem arises for hard to dissolve drugs. In the case of conventional drugs, some drugs are relatively insoluble in gastrointestinal fluids. If the extent of solubility is low, this may cause incomplete and/or erratic absorption. If the rate of solubility is low, then absorption will most probably be erratic on an intra-patient and inter-patient basis. Peptide drugs can be water soluble, and these are not as problematic as insoluble peptides. Like conventional drugs, insoluble peptides typically exhibit incomplete or low extent of absorption and erratic absorption or bioavailability.

The primary difficulty involved in delivering peptides orally is their degradation by hydrolysis and proteolytic enzymes. There are two basic approaches to eliminating this difficulty. The first is an "enteric" coating that releases the drug only in neutral to basic pH (usually pH 6–8), like that found in the intestine, so that the peptide is not exposed to gastric juices. However, this approach alone is not sufficient to protect the peptide since proteolytic enzymes exist in the upper intestinal tract, and degradation of the drug can still occur. The other approach is to incorporate the peptide in a hydrophobic material so that aqueous fluids cannot penetrate the system. It is important to select a hydrophobic material that can erode or slowly dissolve in the intestinal tract so that the drug is released. In this way, the peptide is protected from proteolytic enzymes. In addition, it is possible to combine the two approaches. See, for example, with relation to the enteric coating approach.

However, there are inherent difficulties with the approaches outlined above. First, many drugs are released too slowly from hydrophobic systems. Also, some peptides will partition into the hydrophobic phase so that they will not be fully released from these systems. Thus, both the rate and extent of drug release are crucial components of any drug delivery system, and are even more important for many peptide drugs.

In accordance with the present invention there is provided a pharmaceutical composition comprising a pharmaceutical agent incorporated into a pharmaceutical carrier emulsion comprised of a hydrophobic material selected from the group consisting of a long chain carboxylic acid, long chain carboxylic acid ester, long chain carboxylic acid alcohol and mixtures thereof emulsified with a hydrophilic material.

The composition is used for convenient delivery of drugs. A wide range of active agents can be administered in the composition, including antibiotics, antimicrobials, antineoplastics, antivirals, cardiovascular and renal agents, immunosuppressive and immunostimulatory agents, and CNS active agents, but it is of particular value for peptides. Microemulsion, compared with normal (macro-) emulsions, form easily, even spontaneously, without high energy input, and scale-up easily. They are stable, with long shelf life, and, being translucent, are easy to monitor spectroscopically. They have low viscosity for easy transport and mixing. Drug solubilization, protection against enzyme hydrolysis and, therefore, oral bioavailability, particularly for peptides, are enhanced.

In one embodiment, the hydrophobic material forms the discontinuous phase and the hydrophilic material forms the continuous phase in which the hydrophobic material is emulsified (oil-in-water). The hydrophobic discontinuous phase and the hydrophilic continuous phase can each independently be solid, semisolid or liquid. The pharmaceutical agent may be dispersed or incorporated into the hydrophobic material, the hydrophilic material or in both the hydrophobic and hydrophilic materials. Preferably the carrier emulsion is a microemulsion.

In another embodiment, the hydrophobic material forms the continuous phase and the hydrophilic material forms the discontinuous phase in which the hydrophobic material is emulsified(water-in-oil). The hydrophobic discontinuous phase and hydrophilic continuous phase can each independently be solid, semisolid or liquid. The pharmaceutical agent may be dispersed or incorporated into the hydrophobic material, the hydrophilic material or in both the hydrophobic and hydrophilic materials. Preferably the carrier emulsion is a microemulsion. In this embodiment the invention provides a pharmaceutical preparation comprising a water-in-oil emulsion, preferably a microemulsion, containing an oil phase (such as a long chain carboxylic acid or ester or alcohol thereof), a surface active agent (such as poloxamer) and an aqueous phase containing the drug. The advantage of using a water-in-oil microemulsion is that it has the ability to dissolve relatively large amounts of polar solutes in an overall oily environment, creating an oral delivery system for peptide and protein drug molecules.

Figure 1:
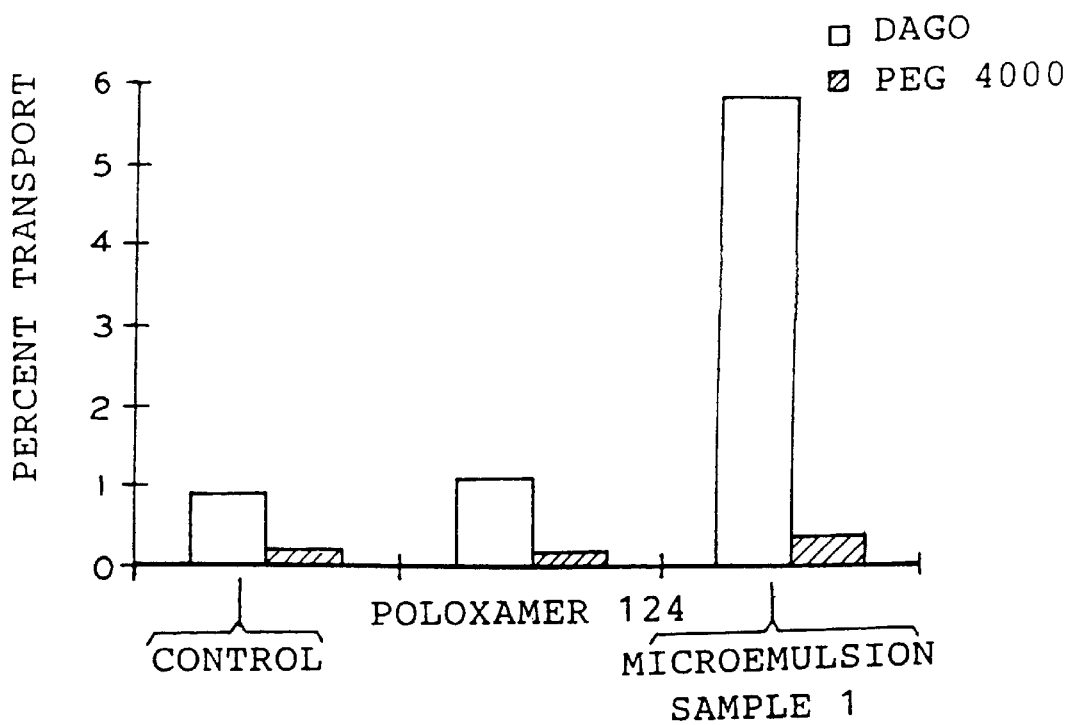
FIG. 1 shows the results of the experiments described in Example 8.

An emulsion is a dispersed system containing at least two immiscible liquid phases, a hydrophobic phase and a hydrophilic phase. The emulsion comprises the dispersed phase, the dispersion phase and an emulsifying agent or surfactant agent, except when the hydrophobic material is a "self-emulsifying" ester, whereby it is possible to produce an emulsion without a separate emulsifying agent. Usually one of the two immiscible liquids is an oil while the other is aqueous. Which phase becomes the dispersed phase depends on the relative amounts of the two liquid phases and which emulsifying agent is selected. Therefore, an emulsion in which the oil is dispersed as droplets throughout the aqueous phase is called an oil-in-water (o/w) emulsion and vice versa. The term "colloidal" refers to emulsions in which the dispersed phase is of very fine particles, usually less than about 1 mm in size. A "microcolloid" is an emulsion wherein the dispersed particles are usually about 100 um or less in size. Cosurfactants are also common components of microcolloids and are simply surfactants included in addition to the primary surfactant.

A "microemulsion" is an optically isotropic and thermodynamically or kinetically stable liquid emulsion. Microemulsions are composed of an oily phase, an aqueous phase, a surfactant and sometimes a cosurfactant. They are ideal for oral drug delivery systems since they are homogeneous, thermodynamically stable, have uniform droplet sizes of approximately 200 Å and are optically clear. A water-in-oil microemulsion, in particular, has small aqueous phase droplets, uniformly dispersed in a continuous oil phase. Therefore, over a wide range of peptide solubilities the peptide is protected from proteolytic enzymes that are soluble in the digestive fluids. In general, the chemical structure of peptides dictates that they be at least somewhat if not mostly water soluble, and thus will be located inside the water droplet or very near the surface of the droplet of the water-in-oil microemulsion system. Thus, the outer oily phase of the microemulsion will prohibit migration of proteolytic enzymes through the delivery system. The outer oily phase of the microemulsion is also able to incorporate into the intestinal cell matrix, thus creating channels (either para cellularly or transcellularly) through which the peptide drug could pass.

Therefore it is important to select a hydrophobic material that can erode or slowly dissolve in the intestine or become incorporated into the intestinal cell matrix so that the drug is released. In addition, it is possible to combine the two approaches, for example, with relation to the enteric coating approach.

The oil-in-water emulsions of the invention are generally made by adding hot (70–80° C.) hydrophobic phase (smaller by weight) to hot (70–80° C.) hydrophilic phase (larger by weight) forcing inversion of the surface active agent to form a disperse emulsion of unaggregated dispersed phase particles. This produces an emulsion when processed under suitable shear. The drug is usually added with the hydrophobic material when it is an organic molecule that is poorly soluble in aqueous media. The drug is usually added after the emulsion has been formed and allowed to cool when it is a peptide. The drug in emulsion formulation is then filled into a soft or hard gelatin capsule, tablet or other oral dosage form.

In accordance with the present invention certain hydrophobic materials, when emulsified in a continuous phase of a hydrophilic material provide enhanced absorption capabilities for oral delivery of peptide drugs and drugs that are poorly soluble in aqueous media. In accordance with the invention, these materials are selected from the group consisting of long chain carboxylic acids, long chain carboxylic acid esters, long chain carboxylic acid alcohols and mixtures thereof.

Further, certain materials, when combined in accordance with the invention to form a water-in-oil microemulsion, give enhanced absorption capabilities. These materials are an oily phase, composed of long chain fatty acids or esters or alcohols thereof, an aqueous phase composed primarily of water, and a surface active agent, primarily of the non-ionic block copolymer type, that are mixed together to form a water-in-oil microemulsion.

The long chain carboxylic acids, generally contain from 4–36 carbon atoms and preferably contains at least 12 carbon atoms, most preferably 12 to 22. In some cases this carbon chain is fully saturated and unbranched, while others contain one or more double bonds. They can have saturated, unsaturated, branched or straight chain hydrocarbon chains. A few contain 3-carbon rings or hydroxyl groups. The compounds are not surface active. They are poorly soluble in water and the longer the acid chain and the fewer the double bonds, the lower the solubility in water. The carboxylic acid group is polar and ionized at neutral pH. This accounts for the slight solubility of short-chain acids in water.

Examples of such acids are those ranging from $C_{16}$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocaboxyic acids. Examples of these are linoleic acid, ricinoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate, glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company) d-alpha tocopherol polyethylene glycol 1000 succinate (Vitamin E TPGS, Eastman Chemical Company); mixtures of mono- and di-glyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$–$C_{30}$ cholesterol/lavosterol esters; and sucrose long chain carboxylic acid esters.

Examples of the self-emulsifying long chain carboxylic acid esters include those from the groups of stearates, palmitates, ricinoleates, oleates, behenates, ricinolenates, myristates, laurates, caprylates, and caproates.

The alcohols useful in the invention are exemplified by the hydroxyl forms of the carboxylic acids exemplified above and also stearyl alcohol.

Additives to the carboxylic acid/alcohol phase can be used to create a solid at room temperature. This addition affords the opportunity to make better use of enteric coatings. Examples of such additives are glycerol behenate, cetyl alcohol, stearic acid, sorbitan ester derivatives such as sorbitan stearate, sobitan isostearate, polyethylene glycol 1000 to 6000.

The types of protective or sustained release coatings that can be used include, but are not limited to, ethylcellulose, hydroxypropylmethylcellulose, hydroxypropylcellulose, hydroxyethylcellulose and esters of methacrylic and ethacrylic acid (Eudragit RL, RS, and NE polymer products, Rohm Pharma, Darmstadt, Germany). The enteric protective materials or coatings can be, for example, cellulose acetate pthalate, hydroxypropylmethylcellulose pthalate, ethylvinylacetate pthalate, polyvinylacetate pthalate and esters of methacrylic and ethacrylic acid (Eudragit S, Budragit L and Eudragit E30D, Rohm Pharma, Darmstadt, Ger.).

The composition or preparation of the invention can further include a surfactant, or a mixture of two or more surfactants. A surfactant is an amphiphilic molecule consisting of a hydrophobic tail and a hydrophilic head. These molecules possess distinct regions of both hydrophilic and hydrophobic character. The hydrophobic tail can be a hydrocarbon or fluorocarbon chain of 8 to 18 carbon atoms. They are long chain molecules such as, for example, soaps or detergents. Surfactants accumulate at the hydrophilic/hydrophobic (water/oil) interface and lower the surface tension. Surface active agents or surfactants are long chain molecules, such as soaps and detergents, which accumulate at the hydrophilic/hydrophobic(water/oil) interface and lower the surface tension at the interface. One effect of a reduced surface tension is the stabilization of the emulsions. This is because molecules with both polar and non-polar groups become oriented such that the hydrocarbon tail embeds itself into the hydrophobic phase and the hydrophilic head protrudes into the hydrophilic phase. Where the hydrophobic composition or other component of the preparation includes a surface-active agent, such as a surfactant, it is usually present in amounts of about 0.05% to 50.0% weight/weight of the hydrophobic composition with a preferred range of 1.0% to 3.0% (w/w). Preferred surfactants include, for example, the Tween(polyoxyethylene sorbate) family of surfactants(ICI, Wilmington Del.), the Span (sorbitan long chain carboxylic acid esters) family of surfactants(ICI), the Pluronic(ethylene or propylene oxide block copolymers) family of surfactants (BASF, Parsippany N.J.), the Labrasol, Labrafil and Labrafac(each polyglycolyzed glycerides) families of surfactants(Gappe Fosse, St. Priest, France), sorbitan esters of oleate, stearate, laurate or other long chain carboxylic acids, poloxamers (polyethylene-polypropylene glycol block copolymers), other sorbitan or sucrose long chain carboxylic acid esters, mono and diglycerides, PEG derivatives of caprylic/capric triglycerides and mixtures thereof.

The drugs to be incorporated individually or as combinations in the pharmaceutical preparations of the invention are those having less than about 80% oral bioavailability. The term "bioavailability" as used here means the rate and extent of systemic absorption of a drug from the oral route of administration.

In one aspect, the drug is a polypeptide, usually of less than about 15 amino acids. Examples include cyclosporin, angiotensin I, II and III, encephalins, enkephalins and their analogs, ACTH, antiinflammatory peptides I, II, III, bradykinin, calcitonin, cholecystikinin (CCK) fragments 26–33 and 30–33, pre/pro CCK (V-9-M), β-endorphin, dinorphin, leucokinin, leutinizing hormone releasing hormone (LHRH), neurokinins (e.g. neurokinin A), somatostatin, substance P, thyroid releasing hormone (TRH), vasopressin, fibrinogen receptor antagonists (arginine-glycine-aspartic acid containing peptides) which are platelet aggregation inhibitors, growth hormone releasing peptides (GHRP), insulin, LH-RH releasers and inhibitors, endothelins, artial natreutetic factor, gastrin, cytoprotectives, MSH modulators, or elastase or growth factors and cytokines, renin inhibitors, and HIV protease inhibitors.

In another aspect, the drug is an organic molecule that is poorly soluble in aqueous media. These organic molecules usually have a molecular weight (m.w.) of less than about 1,000 daltons, and usually less than about 600 daltons. Examples include cabamazepine, griseofulvin, angiotensin converting enzyme inhibitors, flutamide, nifedipine, acyclovir, gancyclovir, indomethacin, naproxen, estrogens, testosterones, steroids, phenytoin, ergotamines and cannabinoids.

Preferred drugs that meet these criteria include, but are not limited to, angiotensin I, II and III, ACTH, anti-inflammatory peptides 1, 2 and 3, bradykinin, cyclosporin, calcitonin, CCK fragments 26–33 and 30–33, Pre- pro-CCK (V-9-M), beta-endorphin, dynorphin, leucokinin, LHRH, neurokinin A, somatostatin, substance P, TRH, vasopressin, enkephalin analogues, ebiratide, galanin, and growth hormone releasing hormone.

In accordance with the invention, drugs are incorporated into the microemulsions by admixture using conventional mixing devices and homogenizers used for semi-solid ointments and lotions, with agitation at speeds common to emulsified products such as creams and emulsions. Examples of common equipment employed are propeller or turbine mixers, homogenizers, colloid mills, ultrasonic mixers and microfluidizers. Examples of such brand name mixing equipment are Lee Kettle, Gaulin mixer and Stephan. The shear of the agitation should be sufficient to form a stable dispersion, but not too great to cause degradation of the drug. The shear forces will form aggregates that have diameters ranging from 100–500 angstroms. Suitable homogenizers are available from Micromedics, Inc., Silverson, and APV Crepaco, Arde Barinco. Stephen and Fryma mixers can also be employed with suitable vacuum to prevent formation of bubbles. Monitoring and evaluation of pH, viscosity, specific gravity and aggregate sizes are necessary.

Using these devices, the mixture of drug in the hydrophobic material (in the oil-in-water embodiment) is formed into particles, e.g. beads or spheres, by spray-congealing or "prilling". This process uses a spray nozzle which atomizes the material in a cooling tower or chamber. As the material is sprayed, surface tension causes a uniform spherical bead to be formed. As the bead falls through the cooling chamber, it hardens into a stable, intact sphere.

The particles generally have a particle size of from 0.5 microns to 100 microns. It is preferred to reduce the size of the sphere as much as possible, most preferably below 10 microns. Optionally, the particles are coated with a sustained-release coating and/or an enteric coating to modify the rate of drug release from the particles.

The particles can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. Because of their hydrophobic nature, the particles should not need a lubricant, but one can be added if necessary by using polyethylene glycol, leucine, glyceryl behenate, magnesium stearate or calcium stearate.

The particles may also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (Avicel), soy polysaccharide (Emcosoy), pre-gelatinized starches (STARCH 1500, National 1551), and polyethylene glycols (Carbowax). The materials should be present in the range of 5–75% (w/w), with a preferred range of 25–50% (w/w).

In addition, disintegrants are added in order to disperse the particles once the tablet is ingested. Suitable disintegrants include, but are not limited to: cross-linked sodium carboxymethyl cellulose (Ac-Di-Sol), sodium starch glycolate (Explotab, Primojel), and cross-linked polyvinylpolypyrrolidone (Plasdone-XL). These materials should be present in the range of 3–15% (w/w), with a preferred range of 5–10% (w/w).

Lubricants are also added to assure proper tableting, and these can include, but are not limited to: magnesium stearate, calcium stearate, stearic acid, polyethylene glycol, leucine, glyceryl behanate, and hydrogenated vegetable oil. These lubricants should be present in amounts from 0.1–10% (w/w), with a preferred range of 0.3–3.0% (w/w).

Tablets are formed, for example, as follows. The particles are introduced into a blender along with Avicel, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

The capsule or tablet can also be enteric coated. Either the particles can be enteric coated (Ph sensitive) and released in the stomach or the capsule or tablet can be enteric coated (thereby releasing the particles in the intestine), in which case the particles need not be so coated. To use only a sustained release coating on the particle one would also need an enteric coated capsule or tablet. There are three approaches here. First, there is the uncoated hydrophobic particle in an enteric coated capsule. Second, there is the sustained release coated particle within an enteric coated capsule or tablet. Third, there is the enteric coated particle enclosed within a regular soft gelatin capsule or uncoated tablet.

The capsule may be further processed to provide gastric protection by enterically coating the capsule. When the contents of the capsule are released into the gastrointestinal milieu, it spontaneously forms a microcolliodal emulsion with the gastrointestinal fluid. The gastrointestinal fluid acting as the aqueous phase.

Microemulsions are generally formed by adding the aqueous phase, oily phase, and surfactant to a suitable vessel and mixing. If any of the ingredient is a solid, it should be added to a liquid phase in which it is soluble and heated to dissolve. For example, if the surfactant is a solid, and it is soluble in the oily phase, then it should be dissolved completely, then followed with aqueous phase, etc. On the other hand, if the surfactant is soluble in the aqueous phase, then it should first be added to the aqueous phase, dissolved completely, followed by the oily phase. Appropriate mixing devices as mentioned above can be employed for this purpose.

The preparation of an oil-in-water emulsion based system, requires that the drug be diapered into the hydrophobic material as described above, with the aqueous phase being added in the presence of surfactant or self-emulsifying hydrophobic long chain carboxylic acid ester. This procedure under suitable shear forms a microemulsion. This emulsion is then filled into a soft or hard gelatin capsule. The capsule may be further processed to provide gastric protection by enterically coating the capsule.

Examples 1–7 describe formulations that illustrate the oil-in-water embodiment of the invention.

EXAMPLE 1

| Phase | Ingredients | % W/W |
|---|---|---|
| B | Carbamazepine | 5 |
| B | Glyceryl Monostearate | 5–60 |
| A | Polysorbate 80 | 5 |
| A | Oleic Acid | 2–10 |
| A | Water | q.s. to 100 |

The ingredients of each phase are heated separately to 70–80° C. Phase B is added to phase A while mixing in an appropriate mixing device. The mixture is then cooled to room temperature. The resultant emulsion is ready to be incorporated into any suitable oral delivery dosage form.

EXAMPLE 2

| Phase | Ingredients | % W/W |
|---|---|---|
| B | Cyclosporine | 5 |
| B | Medium Chain Mono and Diglycerides | 17 |
| A | Polysorbate 80 | 5 |
| B | Oleyl Alcohol | 2–10 |
| A | Water | q.s. to 100 |

The procedure is the same as that described in Example 1.

EXAMPLE 3

| Phase | Ingredients | % W/W |
|---|---|---|
| B | ACE Inhibitor | 5 |
| A | Peg-25 Glyceryl Trioleate | 30–60 |
| B | Oleyl Alcohol | 2–10 |
| A | Water | q.s. to 100 |

The procedure is the same as that described in Example 1.

EXAMPLE 4

| Phase | Ingredients | % W/W |
|---|---|---|
| B | Somatostatin | 5 |
| B | Medium chain Mono and Diglycerides | 17 |
| A | Polysorbate 80 | 5 |
| A | Oleic Acid | 2–10 |
| A | Water | q.s. to 100 |

The procedure is the same as that described in Example 1.

EXAMPLE 5

| Phase | Ingredient | % W/W |
|---|---|---|
| A | Enkephalin | 5 |
| B | Oleyl alcohol | 14 |
| C | Sorbitan Monooleate | 14 |
| D | Polysorbate 80 | 14 |
| E | Water | q.s. 100 |

Phase A and B are mixed together, then C through E are added in any order with stirring.

EXAMPLE 6

| Phase | Ingredients | % W/W |
|---|---|---|
| A | TRH | 5 |
| B | d-Alphatocopheryl Polyethylene glycol 1000 succinate | 10 |
| C | d-alpha Tocophenol acetate | 3 |
| D | Oleyl alcohol | 2–10 |
| H | Water | q.s. 1000 |

Ingredients B and C are heated to >40° C. and mixed. Ingredient A is then added. Ingredient D is then added to the above and the resultant mixture is then added to ingredient E, which is at ~7–80° C. This is then mixed while cooling.

EXAMPLE 7

| Phase | Ingredients | % W/W |
|---|---|---|
| A | Ebiratide | 5 |
| B | Acetylated monoglycerides | 10 |
| C | Dioctyl sodium sulfosyccinate | 10 |
| D | Apricot Kernal oil | 10 |
| E | Water | q.s. 100 |

Phase A is dissolved into D, then the other ingredients are added with gentle stirring.

Examples 8–12 describe formulations that illustrate the water-in-oil embodiment of the invention and demonstrate in vitro delivery enhancement across Caco-2 cells using the model peptide DAGO enkephalin.

Preparation of Caco-2 Cells

An in vitro model of intestinal epithelium, the Caco-2 human colon carcinoma cell line is used as the preliminary assay system. These cells differentiate in culture to form a confluent monolayer with the barrier properties of normal intestinal epithelium. Cells are grown on permeable membranes in a transport system with discrete, accessible liminal and basil compartments.

The time course of differentiation, barrier formation, and active transport of glucose has been determined. Cells have been found to form brush borders and tight junctions between cells as demonstrated by electron microscopy, enzyme assays, and reversible opening of calcium dependent junctions by chelation. Transport of labeled peptides is measured from luminal to basal compartments with time. Microemulsions are compounded using physiologic buffers vs. the aqueous phase and applied to the luminal surface of the cell monolayer. Appearance of peptides is quantified and percent transport per hour per square centimeter calculated and compared to buffer alone.

EXAMPLE 8

| Ingredients | % |
|---|---|
| Poloxamer 124 | 27.0 |
| Linoleic acid | 63.1 |
| Aqueous phase | 9.9 |

General Procedure

Mix ingredients well using one of the above mentioned appropriate mixing devices in a suitable container to form an optically clear solution. Add 10 mM DAGO enkephalin and apply solution to Caco-2 cells. The results are shown in FIG. 1.

EXAMPLE 9

| Ingredients | % |
|---|---|
| Poloxamer 124 | 19 |
| Oleyl alcohol | 75.9 |
| Aqueous phase | 5.1 |

General Procedure

Figure 2:
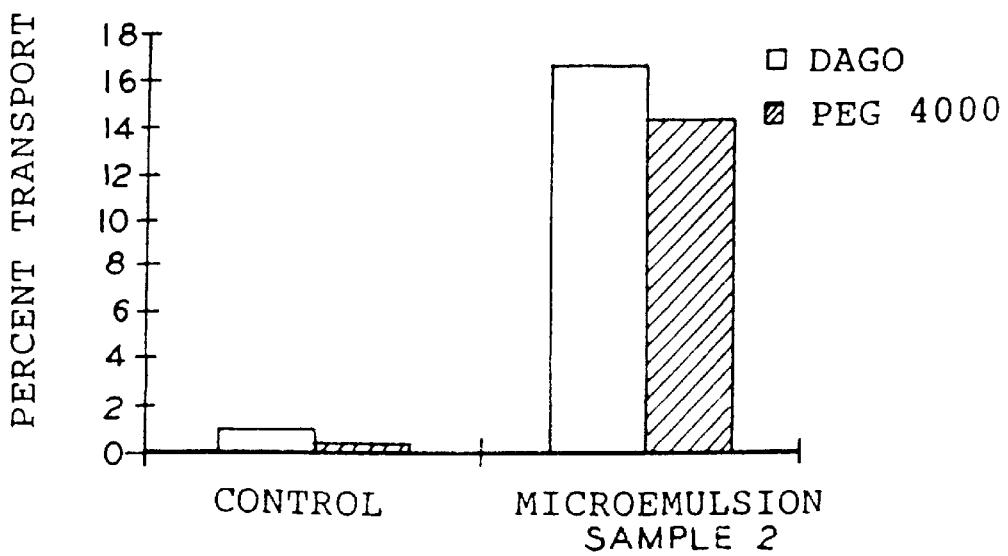
FIG. 2 shows the results of the experiments described in Example 9.

Mix ingredients well using one of the above mentioned appropriate mixing devices in a suitable container to form an optically clear solution. Add 10 mM DAGO enkephalin and apply solution to Caco-2 cells. The results are shown in FIG. 2.

EXAMPLE 10

| Ingredients | % |
|---|---|
| Poloxamer 124 | 27.0 |
| Oleic acid | 63.1 |
| Aqueous phase | 9.9 |

General Procedure

Figure 3:
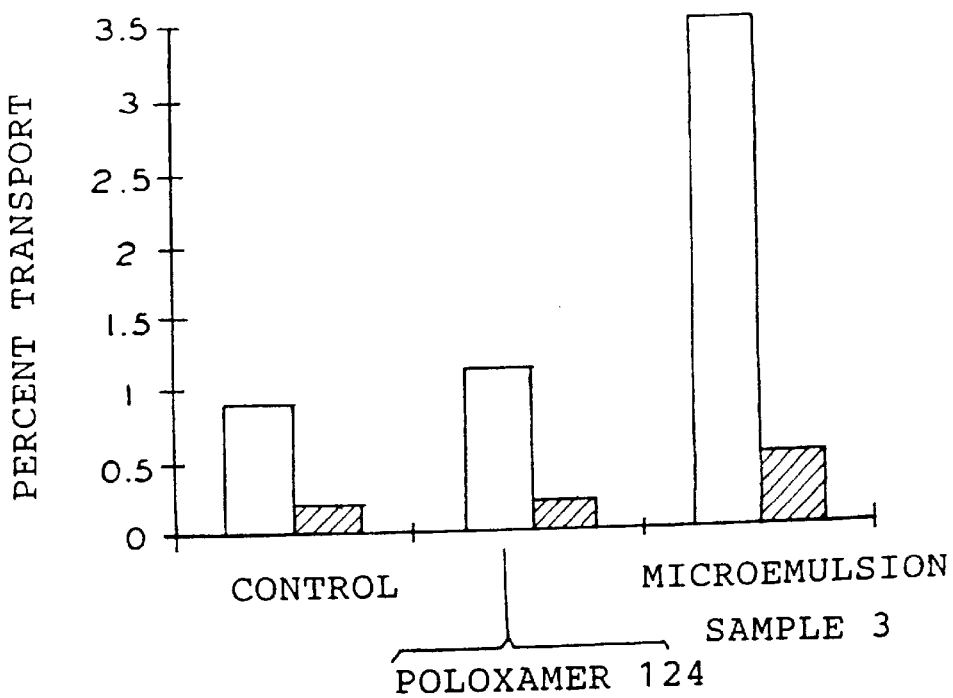
FIG. 3 shows the results of the experiments described in Example 10.

Mix ingredients well using one of the above mentioned appropriate mixing devices in a suitable container to form an optically clear solution. Add 10 mM DAGO enkephalin and apply solution to Caco-2 cells. The results are shown in FIG. 3.

EXAMPLE 11

| Ingredients | % |
|---|---|
| Poloxamer 124 | 27.0 |
| Linoleic acid | 61.7 |
| Aqueous phase | 9.9 |
| Behenic acid | 1.35 |

General Procedure

Figure 4:
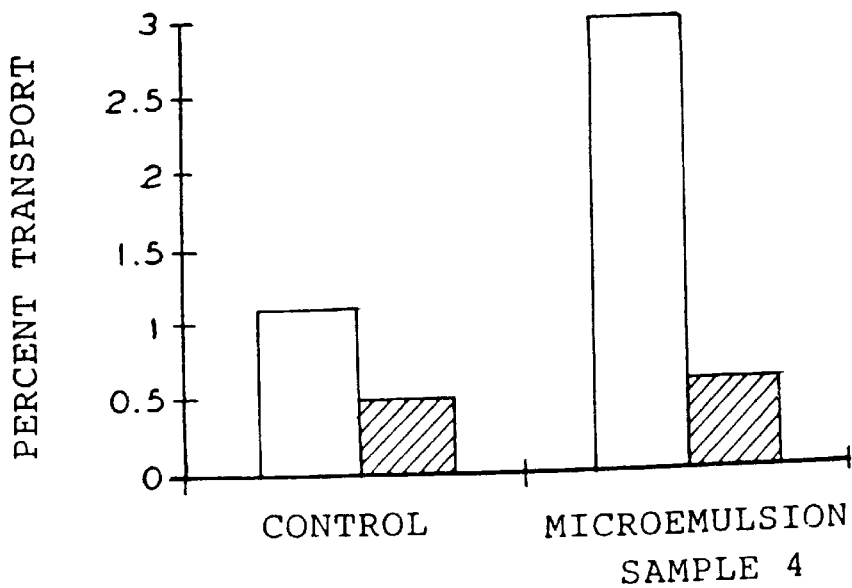
FIG. 4 shows the results of the experiments described in Example 11.

Melt behenic acid in linoleic in a suitable container at 50–80° C. Cool to 40° C., add remaining ingredients and mix well. Add 10 mM DAGO enkephalin and apply solution to Caco-2 cells. This microemulsion is a solid at room temperature. The results are shown in FIG. 4.

EXAMPLE 12

| Ingredients | % |
|---|---|
| Poloxamer 105 | 27.0 |
| Linoleic acid | 63.1 |
| Aqueous phase | 9.9 |

General Procedure

Figure 5:
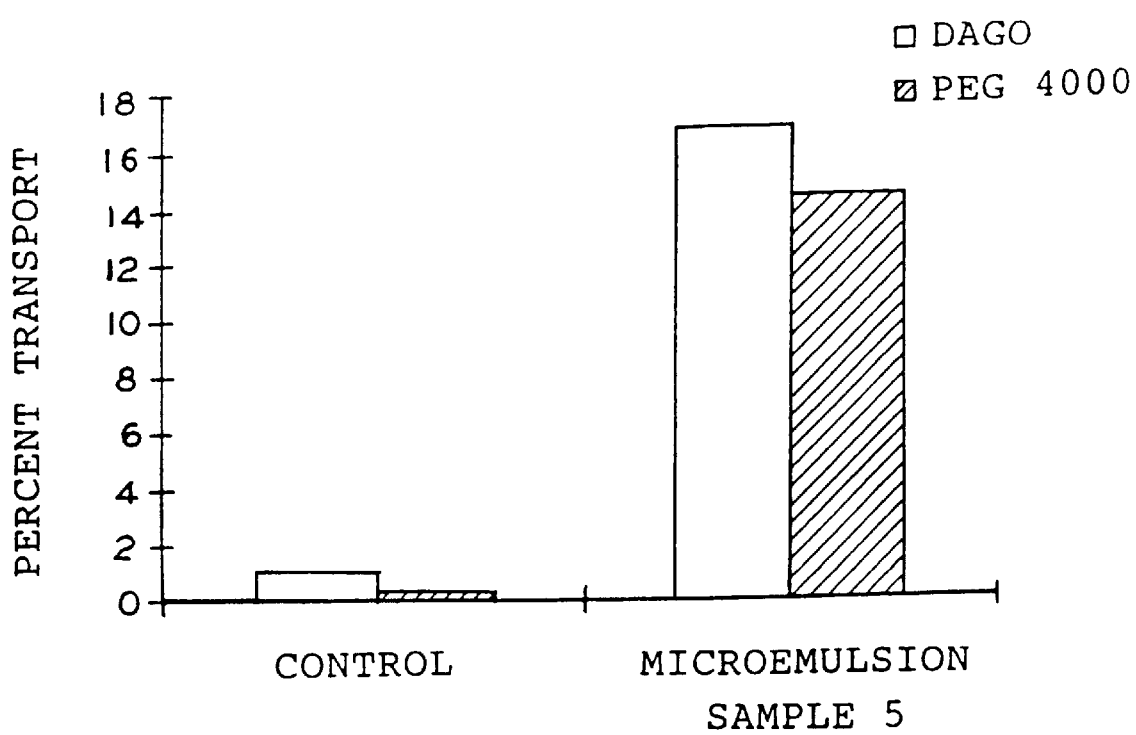
FIG. 5 shows the results of the experiments described in Example 12.

Mix ingredients well using one of the above mentioned appropriate mixing devices in a suitable container to form an optically clear solution. Add 10 mM DAGO enkephalin and apply solution to Caco-2 cells. The results are shown in FIG. 5.

EXAMPLE 13

Pluronic L44/Fatty Acid or Alcohol/Hank's Microemulsion System for the Transport of Peptides Across Caco-2 Cells Microemulsion system formulations containing Pluronic L44 as the surfactant, Hank's buffer as the aqueous phase and several possible oily phases: oleyl alcohol, oleic acid, and linoleic acid were prepared.

The following materials were used as received to prepare the formulations: Polysorbate 20, 60 and 80 (Tween 20, 60, and 80, ICI Surfactants, Wilmington Del.); glyceryl monooleate/propylene glycol mixture, (Arlacel 186, ICI Surfactants, Wilmington Del.); glyceryl monooleate (Aldo Mo., Lonza Specialty Chemicals, Fair Lawn, N.J.); sorbitan monooleate (Crill 4, Croda, Parsippany, N.J.); oleyl alcohol (Janssen Chemica, Geer, Belgium); and linoleic acid (Emersol 315 Henkel).

Multiple formulations were examined in an effort to utilize the polysorbate surfactant class in a microemulsion vehicle for peptide delivery. The three ICI surfactants Tween 20, 60, and 80 were employed in solution and microemulsion systems with and without cosurfactants. The following present the formulations prepared.

Microemulsion formulations, consisting of Tween 80, Arlacel 186, oleyl alcohol and distilled water and the corresponding Emulsifier (4 parts Tween 80/1 part Arlacel 186) solutions in Hank's buffer were prepared. See Table 1.

TABLE 1

| Ingredients | 72A (%) | 72B1 (%) | 72B2 (%) | B3 (%) | B4 (%) |
|---|---|---|---|---|---|
| Tween 80 | 28.6 | 4 | 8 | 12 | 16 |
| Arlacel 186 | 42.9 | 1 | 2 | 3 | 4 |
| Distilled Water | 25 | 95 | 90 | 85 | 80 |

Formulations with a higher percent of Emulsifier (4 parts Tween 80/1 part Arlacel 186) solutions in Hank's buffer were also prepared See Table 2.

TABLE 2

| Ingredients | 1 | 2 | 3 | 4 |
|---|---|---|---|---|
| Tween 80 | 16 | 20 | 24 | 28 |
| Arlacel | 4 | 5 | 6 | 7 |
| Hank's buffer | 80 | 75 | 70 | 65 |

The formulation for a waterless microemulsion system, consisting of Tween 80, Arlacel 186 and Oleyl alcohol was also prepared. See Table 3.

TABLE 3

| Ingredients | % |
|---|---|
| Tween 80 | 36.9 |
| Arlacel 186 | 36.9 |
| Oleyl alcohol | 26.1 |

The formulations for 10% solutions of Tween 20, 60 and 80 in Hank's buffer each at pH 3.5 and 6.5–7.0 were prepared. In this case, the peptide incorporated for the is vasopressin at 10 $\mu$M. See Table 4.

TABLE 4

| Ingredients | F (%) | G (%) | H (%) | I (%) | J (%) | K (%) |
|---|---|---|---|---|---|---|
| Tween 20 | 10 | — | — | 10 | — | — |
| Tween 60 | — | 10 | — | — | 10 | — |
| Tween 80 | — | — | 10 | — | — | — |
| Hank's buffer | 90 | 90 | 90 | 90 | 90 | 90 |
| Ph | 6.51 | 6.91 | 6.82 | 3.54 | 3.4 | 3.59 |

The formulation for a waterless microemulsion system, consisting of Tween 20, Arlacel 186 and Oleyl alcohol. (Note different surfactant from formula above). See Table 5.

TABLE 5

| Ingredients | 72A (%) | 72B1 (%) | 72B2 (%) | B3 (%) | B4 (%) |
|---|---|---|---|---|---|
| Tween 80 | 28.6 | 4 | 8 | 12 | 16 |
| Arlacel 186 | 42.9 | 1 | 2 | 3 | 4 |
| Distilled Water | 25 | 95 | 90 | 85 | 80 |

Tween 20/Span 20 microemulsion formulations containing linoleic acid as the oily phase were also prepared. See Table 6.

TABLE 6

| Ingredients | 6A | 6B | 6C | 6D | 6E |
|---|---|---|---|---|---|
| Tween 20 | 38.3 | 42.8 | 26.3 | 29 | 47.5 |
| Span 20 | 9.6 | 4.8 | 2.9 | — | — |
| Linoleic Acid | 47.8 | 47.5 | 68.1 | 67.6 | 47.5 |
| Oleic Acid | — | — | — | — | — |
| Oleyl Alcohol | — | — | — | — | — |
| Hank's buffer | 4.6 | 5.1 | 3 | 3.6 | 5.2 |

Tween 20/Span 20 microemulsion formulations containing either linoleic acid, oleic acid or oleyl alcohol were also prepared. See Table 7.

TABLE 7

| Ingredients | 6A | 6B | 6C | 6D | 6E | 13A | 13B | 13C | 13D | 13E | 14B |
|---|---|---|---|---|---|---|---|---|---|---|---|
| Tween 20 | 38.3 | 42.8 | 26.3 | 29 | 47.5 | 38.3 | 42.8 | 26.3 | 29 | 47.5 | 38.9 |
| Span 20 | 9.6 | 4.8 | 2.9 | — | — | 9.6 | 4.8 | 2.9 | — | — | 9.7 |
| Linoleic Acid | 47.8 | 47.5 | 68.1 | 67.6 | 47.5 | | | | | | |
| Oleic Acid | — | — | — | — | — | 47.8 | 47.5 | 68.1 | 67.6 | 47.5 | |

TABLE 7-continued

| Ingredients | 6A | 6B | 6C | 6D | 6E | 13A | 13B | 13C | 13D | 13E | 14B |
|---|---|---|---|---|---|---|---|---|---|---|---|
| Oleyl Alcohol | — | — | — | — | — |  |  |  |  |  | 48.7 |
| Hank's buffer | 4.6 | 5.1 | 3 | 3.6 | 5.2 | 4.6 | 5.1 | 3 | 3.6 | 5.2 | 2.6 |

Three additional microemulsion formulations were also prepared. See Table 8.

TABLE 8

| Ingredients | A (%) | B (%) | C (%) |
|---|---|---|---|
| Pluronic L44 | 26.8 | — | — |
| Labrasol | — | 38.1 | — |
| Labrafac CM-10 | — | 9.5 | — |
| Tween 20 | — | — | 42.8 |
| Span 20 | — | — | 4.76 |
| Linoleic Acid | 63.2 | 47.6 | 47.6 |
| Hank's buffer | 9.9 | 4.76 | 4.76 |

Further formulation efforts with Tween 20 led to a microemulsion in which Span 20 is the cosurfactant. Span 20, or sorbitan monolaurate, acts as an ideal cosurfactant. The oily phase of the new microemulsion systems has also been changed to linoleic acid or oleic acid, which are known to promote peptide transport in other vehicles. Hank's buffer is the aqueous phase and linoleic acid, oleic acid or oleyl alcohol are the oily phases.

EXAMPLE 14

Polysorbate Surfactant Systems and Microemulsions in Oral Peptide Delivery.

The primary research initiative has been to screen and identify systems that increase peptide transport across Caco-2 monolayers. One such system explored contains the surfactant Pluronic L44. Several microemulsion systems formulations have been developed using this surfactant. This example summarizes these systems.

The following materials were used as received to prepare the formulations: Pluronic L44 (BASF, Parsippany, N.J.); oleyl Alcohol (Jannsen Chemica, Geer, Belgium); oleic acid (Emersol 221, Henkel, Emery Group, Cincinnati, Ohio); linoleic acid (Emersol 315, Henkel, Emery Group, Cincinnati, Ohio); and Hank's buffer (Cellgro, Mediatech).

The following tables list formulations prepared for use in transport experiments. The tables give detailed information on the ingredients, amounts and pH, if appropriate.

TABLE 9

Percent Pluronic L44 in Hank's Buffer

| | | Formulation | | |
|---|---|---|---|---|
| Ingredient | % | G % | H % | I % |
| Pluronic L44 | 0 | 7.5 | 15 | 30.0 |
| Hank's buffer | 100 | 92.5 | 85.0 | 70.0 |

TABLE 10

Formulation of Pluronic Microemulsions

| | Formulation | |
|---|---|---|
| Ingredients | D % | E % |
| Pluronic L44 | 26.8 | 30 |
| Oleyl alcohol | 62.5 | 70 |
| Hank's | 10.7 | 0 |

TABLE 11

Microemulsions Containing Pluronic L44, Oleyl Alcohol, Hank's Buffer and Solutions of Pluronic F68 and F108

| Ingredients | Formulations | | | Ratio Pluronic L44 to Oleyl Alcohol |
|---|---|---|---|---|
|  | A | B |  |  |
| Pluronic L44 | 27 | 28.3 |  | 3 |
| oleyl alcohol | 63.1 | 66 |  | 7 |
| Hank's buffer | 9.9 | 5.7 |  |  |
|  | C | D | E |  |
| Pluronic L44 | 41.8 | 44.76 | 47.44 | 5 |
| oleyl alcohol | 41.8 | 44.76 | 47.44 | 5 |
| Hank's buffer | 16.3 | 10.47 | 5.12 |  |
|  | F | RATIO | G |  |
| Pluronic L44 | 19 | 2 | 34.2 | 4 |
| oleyl alcohol | 75.9 | 8 | 51.3 | 6 |
| Hank's buffer | 5.1 |  | 9.4 |  |
|  | H | I | J |  |
| Pluronic F68 | 30 | 15 | 7.5 |  |
| Hank's buffer | 70 | 85 | 92.5 |  |
|  | L | M | N+ |  |
| Pluronic F108 | 15 | 7.5 | 3.75 |  |
| Hank's buffer | 85 | 9.25 | 9.625 |  |

TABLE 12

Microemulsions with Pluronic L44 to Oily Phase Ratio of 3:7. Oily phases are either oleic acid or linoleic acid. Percent aqueous phase (Hank's buffer) varies changes from about 10% to about 14%.

| | % |
|---|---|
| Formulation A | |
| Pluronic L44 | 27 |
| oleic acid | 63.1 |
| Hank's buffer | 9.9 |

TABLE 12-continued

Microemulsions with Pluronic L44 to Oily Phase Ratio of 3:7. Oily phases are either oleic acid or linoleic acid. Percent aqueous phase (Hank's buffer) varies changes from about 10% to about 14%.

|  | % |
| --- | --- |
| Formulation B | |
| Pluronic L44 | 27 |
| linoleic acid | 63.1 |
| Hank's buffer | 9.9 |
| Formulation C | |
| Pluronic L44 | 25.8 |
| oleic acid | 60.1 |
| Hank's buffer | 14.1 |
| Formulation D | |
| Pluronic L44 | 25.8 |
| linoleic acid | 60.1 |
| Hank's buffer | 14.1 |

TABLE 13

A) Pluronic L44/linoleic acid/Hank's buffer and B) Pluronic L44/oleic acid/Hank's buffer microemulsions at pH 6.5. The pH was increased using NaOH pellets.

| Ingredients | % |
| --- | --- |
| Pluronic L44 | 27 |
| linoleic acid | 63.1 |
| Hank's buffer | 9.9 |
| NaOH pellets pH 6.5 | |
| Pluronic L44 | 27 |
| oleic acid | 63.1 |
| Hank's buffer | 9.9 |
| NaOH pellets pH 6.5 | |

TABLE 14

Formulations of Pluronic L44/linoleic acid/Hank's buffer at various pH's. The pH was increased using NaOH pellets.

| | PD0002-9D1 Formulations PD0002- | | |
| --- | --- | --- | --- |
| Ingredients | 9D1 | 9D2 | 9D3 |
| Pluronic L44 | 27 | 27 | 27 |
| linoleic acid | 63.1 | 63.1 | 63.1 |
| Hank's buffer | 9.9 | 9.9 | 9.9 |
| pH | 3.5 | 4.5–5.0 | 6.0–6.5 |

PD0002-9D2: Same As D1, but pH 4.5–5.0
PD0002-9D3: Same As D1, but pH 6.0–6.5

| | PD0002-9E1 Formulations PD0002- | | |
| --- | --- | --- | --- |
| Ingredients | 9E1 | 9E2 | 9E3 |
| Pluronic L44 | 27 | 27 | 27 |
| oleic acid | 63.1 | 63.1 | 63.1 |
| Hank's buffer | 9.9 | 9.9 | 9.9 |
| pH | 3.5 | 4.5–5.0 | 6.0–6.5 |

PD0002-9E2: Same As E1, but pH 4.5–5.0
PD0002-9E3: Same As E1, but pH 6.0–6.5

TABLE 15

Microemulsion component controls at various pH's: A) Pluronic L44 solutions at pH 2.2, 3.5, 4.8 and 7.9; B) Hank's buffer at pH 2.1, 3.5, 5.0, 7.8; and C) linoleic acid.

| | Date | |
| --- | --- | --- |
| | A | |
| PD0002-10A | 5.4.94 | 26.8% Pluronic L44 in Hank's buffer pH 7.9 |
| PD0002-10B | 5.4.94 | 26.8% Pluronic L44 in Hank's buffer pH 4.8 |
| PD0002-10C | 5.4.94 | 26.8% Pluronic L44 in Hank's buffer pH 3.5 |
| PD0002-10D | 5.4.94 | 26.8% Pluronic L44 in Hank's buffer pH 2.2 |
| | B | |
| PD0002-11A | 5.4.94 | 100% HANK'S BUFFER pH 7.8 |
| PD0002-11B | 5.4.94 | 100% HANK'S BUFFER pH 5.0 |
| PD0002-11C | 5.4.94 | 100% HANK'S BUFFER pH 2.1 |
| PD0002-11D | 5.4.94 | 100% HANK'S BUFFER pH 3.5 |
| | C | |
| PD0002-10E | 5.4.94 | 100% LINOLEIC ACID |

TABLE 16

Pluronic L44/linoleic acid/Hank's buffer microemulsion at pH 3.5, 5.0 and 7.0.

| | PD0002-12 | | |
| --- | --- | --- | --- |
| Ingredients | A | B | C |
| Pluronic L44 | 27 | 26.8 | 25.5 |
| linoleic acid | 63.1 | 62.6 | 59.6 |
| Hank's buffer | 9.9 | 9.8 | 15 |
| pH | 3.5–3.8 | 4.9 | 7 |

EXAMPLE 15

Variations of the Pluronic L44/Linoleic Acid/ Hank's Microemulsion System

The following materials were used as received to prepare the formulations: Pluronic L44 (BASF, Parsippany, N.J.); linoleic Acid (Emersol 315, Henkel, emery Group, Cincinnati, Ohio); oleic Acid (Emersol 221, Henkel, Emery Group, Cincinnati, Ohio); linolenic Acid (Aldrich, Milwaukee, Wis.); Hank's Buffer (Cellgro, Mediatech); Ethanol (Alcohol, dehydrated USP, Midwest Grain Products of Illinois, Grain Processing Corp., Muscarine, Id.); and Tween 20 (ICI Surfactants, Wilmington, Del.).

Ricinoleic acid (P-10 Acids, Cas Chem, Bayonne, N.J.) was centrifuged for 30 minutes at 15,000 rpm to remove solids.

The following tables list the formulations prepared. The tables give detailed information on the ingredients and amounts and pH if appropriate.

The general procedure for preparing the microemulsions is as follows: weigh ingredients into reclosable container, shake and sonicate if necessary to remove bubbles.

TABLE 17

Formulations for Pluronic L44/oily phase/Hands buffer microemulsions containing different fatty acids or alcohols as the oily phase and partial substitution of Hands buffer with ethanol.
Formulation: PD0002-

| Ingredients | 19E (%) | 19F (%) | 20E (%) | 27A (%) | 27B (%) | 29A (%) |
|---|---|---|---|---|---|---|
| Pluronic L44 | 27.0 | 27.0 | 27.0 | 27.4 | 26.6 | 27 |
| Hank Buffer | 9.9 | 9.9 | 9.9 | 8.8 | 9.9 | 4.95 |
| oleyl alcohol | 63.1 | 0 | 0 | | | |
| oleic acid | 0 | 63.1 | 63.1 | | | |
| linoleic acid | 0 | 0 | 63.1 | 0 | 63.4 | 63.1 |
| linolenic acid | | | | 0 | 63.4 | 63.1 |
| ricinoleic acid | | | | 0 | 63.4 | 63.1 |
| ethanol | | | | 0 | 0 | 4.95 |

TABLE 18

Formulations for Pluronic L44/fatty alcohol or acid/Hank's buffer containing oleyl alcohol, oleic acid or linoleic acid (PD0002-19E, 19F, 20E respectively), with a substitution of ethanol for part of the Hank's buffer, (PD0002-31A, 31B and 29A) and total substitution of Hank's buffer with ethanol (PD0002-31C) and a change in the ratio of Pluronic L44 to linoleic acid to 2:8 (PD0002-31D).
Formulation PD0002-31

| Ingredients | A % | B % | C % | D % |
|---|---|---|---|---|
| Pluronic L44 | 27 | 27 | 27 | 19 |
| Hank's buffer | 4.95 | 4.95 | N/A | 5.1 |
| oleyl alcohol | 63.1 | N/A | N/A | 75.9 |
| oleic acid | N/A | 63.1 | N/A | N/A |
| linoleic acid | N/A | N/A | 63.1 | N/A |
| ethanol | 4.95 | 4.95 | 9.9 | N/A |

TABLE 19

Formulations of Pluronic L44/linoleic acid/Hank's buffer with varying substitutions of ethanol (PD0002-50A through J) and Pluronic L44/oleyl alcohol/Hank's buffer with ethanol substitutions (PD0002-65).

Formulation PD0002-50

| Ingredients | A | B | C | D | E | F |
|---|---|---|---|---|---|---|
| Pluronic L44 | 27 | 27 | 27 | 27 | 27 | 27 |
| Hank's buffer | 9.9 | 4.95 | 9.9 | 9.9 | 9.9 | 9.9 |
| linoleic acid | 63.1 | 63.1 | 54.1 | 58.6 | 49.6 | 45.1 |
| ethanol | 0 | 4.95 | 9 | 4.5 | 13.5 | 18.02 |

Formulation PD0002-50

| Ingredients | G | H | I | J |
|---|---|---|---|---|
| Pluronic L44 | 27 | 27 | 27 | 27 |
| Hank's buffer | 9.9 | 9.9 | 9.9 | 9.9 |
| linoleic acid | 40.54 | 36 | 31.5 | 27 |
| ethanol | 22.52 | 27 | 31.5 | 36 |

Formulation PD0002-65

| Ingredients | A |
|---|---|
| Pluronic L44 | 27.03 |
| Hank's buffer | 9.91 |
| oleyl alcohol | 54.04 |
| ethanol | 9.01 |

TABLE 20

Addition of water soluble surfactants SLS, sodium cholate and Tween 20 (PD0002-32 A, B, and C, respectively). and addition of an oil soluble additive Eastman SAIB (PD0002-34B) to microemulsion.

Formulation PD0002

| Ingredients | 32 A % | 32 B % | 32 C % | 34 B % |
|---|---|---|---|---|
| Pluronic L44 | 27 | 27 | 27 | 27 |
| Hank's buffer | 9.9 | 9.9 | 9.9 | 9.9 |
| linoleic acid | 63 | 63 | 63 | 63 |
| Solium Lauryl Sulfate | 0.1 | N/A | N/A | N/A |
| sodium cholate | N/A | 0.1 | N/A | N/A |
| Tween 20 | N/A | N/A | 0.1 | N/A |
| Eastman SAIB | | | | 0.111 |

| Formulation PD0002-30 | Ingredients Pluronic | % Pluronic | % Hank's buffer |
|---|---|---|---|
| A | L35 | 0.5 | 95 |
| B | L61 | 0.5 | 95 |
| C | L62 | 0.5 | 95 |
| D | L64 | 0.5 | 95 |
| E | L35 | 1 | 90 |
| F | L61 | 1 | 90 |
| G | L62 | 1 | 90 |
| H | L64 | 1 | 90 |
| I | L44/L61 | 0.25/0.25 | 95 |
| J | L44/L61 | 0.5/0.5 | 90 |
| K | L44 | 5 | 95 |

TABLE 21

Substitutions of Pluronic L44 with L64 and L35 in the microemulsion formulations.
Formulation PD0002-33

| Ingredients | A % | B % |
|---|---|---|
| Pluronic L64 | 27 | N/A |
| Hank's buffer | 9.9 | 9.9 |
| linoleic acid | 63.1 | 63.1 |
| Pluronic L35 | N/A | 27 |

TABLE 22

Pluronic L62/linoleic acid/Hank's buffer microemulsion.
Formulation PD0002-41E

| Ingredients | % |
|---|---|
| Pluronic L62 | 42.87 |
| Hank's buffer | 14.4 |
| linoleic acid | 42.8 |

What is claimed is:

1. A pharmaceutical composition comprising:
   (a) a water-in-oil emulsion comprising:
      (i) a continuous hydrophobic phase comprising at least one member selected from the group consisting of oleic acid, gadoleic acid, erucic acid, linoleic acid, linolenic acid, ricinoleic acid, arachidonic acid, glyceryl esters of such acids, oleyl alcohol and d-alpha-tocopherol polyethylene glycol succinate;
      (ii) a discontinuous aqueous hydrophilic phase;
      (iii) at least one surfactant for dispersing said hydrophilic phase in said hydrophobic phase as a water-in-oil emulsion, wherein said at least one surfactant comprises a member selected from the group consisting of poloxamer 124, a polyglycolized glyceride, sorbitan laurate and polyoxyethylene (20) sorbitan monooleate; and
   (b) a pharmaceutical agent in said aqueous hydrophilic phase.

2. The composition of claim 1 wherein the hydrophobic phase comprises linoleic acid.

3. The composition of claim 1 wherein the hydrophobic phase comprises linoleic acid and oleyl alcohol.

4. The composition of claim 1 wherein the hydrophobic phase comprises glyceryl behenate in combination with a member selected from the group consisting of oleyl alcohol, oleic acid, glyceryl monooleate, linoleic acid, linolenic acid, ricinoleic acid and mixtures thereof.

5. The composition of claim 1 wherein the hydrophobic phase comprises at least one of d-alpha tocopherol polyethylene glycol 1000 succinate.

6. The composition of claim 1 wherein the hydrophobic phase comprises at least one of linoleic acid and further comprises at least one of d-alpha tocopherol polyethylene glycol 1000 succinate or sucrose acetate isobutate.

7. The composition of claim 1 wherein at least one of the surfactants comprises poloxomer 124.

8. The composition of claim 1 wherein at least one of the surfactants comprises a polyglycolized glyceride.

9. The composition of claim 1 wherein at least one of the surfactants comprises polyoxyethylene sorbitan monooleate.

10. The composition of claim 1 wherein the surfactant comprises polyoxyethylene (20) sobitan monooleate and sobitan laurate.

11. The composition of claim 1 wherein the aqueous hydrophilic phase is present in an amount of about 5.1 to about 9.9 weight percent of the emulsion.

12. The composition of claim 1 wherein the aqueous hydrophilic phase comprises a water soluble alcohol.

13. The composition of claim 1 wherein the aqueous hydrophilic phase comprises a balanced saline solution.

14. The composition of claim 1 wherein the surfactant is present in a range of from about 19 to about 27 weight percent of the emulsion.

15. The composition of claim 1 wherein the pharmaceutical agent has less than about 80% bioavailability.

16. The composition of claim 1 wherein the pharmaceutical agent is a polypeptide of up to about 15 amino acids.

17. The composition of claim 16 wherein the polypeptide contains up to about 12 amino acids.

18. The composition of claim 1 wherein the pharmaceutical agent is an organic molecule of less than about 1,000 daltons.

19. The composition of claim 18 wherein the organic molecule is less than about 600 daltons.

20. The composition of claim 1 wherein the hydrophobic phase is present in a range of about 63.1 to about 75.9 weight percent of the emulsion.

21. The composition of claim 1 wherein the emulsion is encapsulated in a capsule comprising an enteric coating material.

22. The composition of claim 21 wherein the enteric coating material is soluble in an acidic aqueous environment.

23. The composition of claim 1 wherein the ester of the hydrophobic phase is a monoglyceryl ester.

24. The composition of claim 1 wherein the hydrophobic phase comprises at least one of linoleic acid and linolenic acid and further comprises at least one of d-alpha tocopherol polyethylene glycol 1000 succinate or sucrose acetate isobutyrate.

* * * * *

UNITED STATES PATENT AND TRADEMARK OFFICE
CERTIFICATE OF CORRECTION

PATENT NO. : 5,897,876
DATED : April 27, 1999
INVENTOR(S) : Rudnic, et al.

It is certified that errors appear in the above-identified patent and that said Letters Patent is hereby corrected as shown below:

On the title page:

Item: [75] Inventors: Edward M. Rudnic, North Potomac, Md.; John A. McCarty, Miami Springs, Fla.; George W. Belendiuk, deceased, late of Potomac, Md.; Beth A. Burnside, Silver Springs, Md.; Charlotte M. McGuinness, Bethesda, Md Item: [62] Continuation of application No. 08/475,322, Jun. 7, 1995, abandoned, which is a continuation of application No. 08/424,521, filed as application No. PCT/US95/03393, Mar. 17, 1995, abandoned, which is a continuation of application No. 08/210,351, Mar. 18, 1994.

In Claim No. 6, Column 19, Line 35: Replace "isobutate" with --isobutyrate--.

In Claim No. 10, Column 20, Lines 2 and 3: Replace "sobitan" with --sorbitan--.

Signed and Sealed this

Seventh Day of December, 1999

Attest:

Attesting Officer

Q. TODD DICKINSON

Acting Commissioner of Patents and Trademarks